United States Patent
Degani et al.

(10) Patent No.: US 7,693,320 B2
(45) Date of Patent: Apr. 6, 2010

(54) THREE TIME POINT LUNG CANCER DETECTION, DIAGNOSIS AND ASSESSMENT OF PROGNOSIS

(75) Inventors: Hadassa Degani, Rehovot (IL); Daphna Weinstein, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 169 days.

(21) Appl. No.: 10/593,887

(22) PCT Filed: Apr. 8, 2005

(86) PCT No.: PCT/IB2005/001252

§ 371 (c)(1),
(2), (4) Date: Aug. 6, 2008

(87) PCT Pub. No.: WO2005/096694

PCT Pub. Date: Oct. 20, 2005

(65) Prior Publication Data

US 2009/0028405 A1    Jan. 29, 2009

Related U.S. Application Data

(60) Provisional application No. 60/560,898, filed on Apr. 8, 2004.

(51) Int. Cl.
G06K 9/00 (2006.01)
A61B 6/00 (2006.01)
(52) U.S. Cl. .......................... 382/131; 382/274; 378/21
(58) Field of Classification Search ................. 382/100, 382/128, 129, 130, 131, 132, 133, 134, 162, 382/163, 164, 165, 166, 168, 181, 189–194, 382/203, 209, 219, 224, 232, 255, 274, 276, 382/305, 312; 378/21, 22, 23; 600/458, 600/420; 250/458.1; 434/262
See application file for complete search history.

(56) References Cited

U.S. PATENT DOCUMENTS 5,255,683 A * 10/1993 Monaghan .................. 600/458
5,579,767 A * 12/1996 Prince ......................... 600/420

(Continued)

OTHER PUBLICATIONS

International Search Report published Jan. 18, 2007 for PCT/IB2005/001252 filed Apr. 8, 2005.

(Continued)

*Primary Examiner*—Seyed Azarian
(74) *Attorney, Agent, or Firm*—Martin Fleit; Paul D. Bianco; Fleit Gibbons Gutman Bongini & Bianco, PL

(57) ABSTRACT

A malignancy classification method and medium for classifying a region of lung tissue are disclosed. The classifying includes: setting time points T1 and T2 measured from injection of a contrast agent. TI represents a wash-in time point for malignant lung tissue at which a first concentration value of the injected contrast agent is substantially equal to or near a peak for injected contrast agent concentration in the region of lung tissue. Patient concentration values of the contrast agent for the area of lung tissue at time points T1 and T2 are obtained, and a malignancy classification for the region of lung tissue is provided by comparing the obtained sample concentration values with a predetermined malignancy profile. A visual representation of the malignancy classification of the region of lung tissue is outputted.

38 Claims, 8 Drawing Sheets

U.S. PATENT DOCUMENTS

| | | | |
|---|---|---|---|
| 6,331,116 B1 * | 12/2001 | Kaufman et al. | 434/262 |
| 7,194,117 B2 * | 3/2007 | Kaufman et al. | 382/128 |
| 7,203,353 B2 * | 4/2007 | Klotz et al. | 382/131 |
| 7,282,723 B2 * | 10/2007 | Schomacker et al. | 250/458.1 |
| 2002/0114503 A1 * | 8/2002 | Klotz et al. | 382/131 |

OTHER PUBLICATIONS

International Preliminary Report on Patentability published Dec. 4, 2006 for PCT/IB2005/001252 filed Apr. 8, 2005.

Written Opinion of the International Searching Authority published Dec. 1, 2006 for PCT/IB2005/001252 filed Apr. 8, 2005.

* cited by examiner

THREE TIME POINT LUNG CANCER DETECTION, DIAGNOSIS AND ASSESSMENT OF PROGNOSIS

CROSS-REFERENCE TO RELATED APPLICATIONS

This application is a national stage of PCT/IB05/01252, filed Apr. 8, 2005, which claims priority to U.S. Provisional Application No. 60/560,898, filed Apr. 8, 2004.

FIELD OF THE INVENTION

The present application relates to medical imaging devices generally, and to methods, systems, and programs of instructions for the evaluation of potentially malignant tissue based on computed tomography (CT) or other such imaging devices.

BACKGROUND OF THE INVENTION

Lung cancer represents one of the major public health problems worldwide. It has been estimated that between 1.3 and 2 million people died from lung cancer in the year 2000. The number of deaths caused by lung cancer exceeds those caused by the next three leading cancers together per year (breast, prostate and colorectal cancers). A decrease in mortality from lung cancer by improved diagnostic means would have an enormous impact on public health as well as reducing health care costs.

Ninety-nine percent of lung tumors are malignant, either primary or secondary. Non-Small Cell Lung Carcinoma (NSCLC) represents 80% of the bronchogenic carcinomas, which include Adenocarcinoma, SCC (Squamous Cell Carcinoma), LCC (Large Cell Carcinoma), and others. Small Cell Lung Cancer (SCLC), sometimes known as Oat Cell Carcinoma, comprises the rest of the cases. SCLC is the most aggressive type with a median survival of 2-4 months. Less common types include Sarcoma, Carcinosarcoma, Blastoma, Lymphoma, and Neuroendocrine tumors such as Carcinoids (both malignant and benign).

Half of patients seeking medical consultation do so when the disease has already advanced beyond surgical treatment. Since the lung parenchyma lacks nerve endings, tumors of the lung can become large before causing local symptoms such as coughing (75%), dyspnea (60%), pain (50%) and hemoptysis (30%). Fever, wheezing, stridor, hoarseness, SVC (Superior Vena Cava) syndrome, Homer syndrome, dysphagia, pleural effusion, and phrenic nerve paralysis may occur as well. Seventy percent of the patients have non-specific symptoms (such as anorexia, myalgia and weight loss), and a minority are asymptomatic. Some present with pneumonia due to bronchial obstruction, and some are diagnosed incidentally by a CXR (Chest X-Ray) assigned for another purpose.

Since pulmonary lesions are commonly encountered in clinical practice, differentiation of benign from malignant tissue remains a challenge for the radiologist. A broad variety of diagnostic techniques is available, with others being developed. Among these diagnostic techniques are the following:

i) CXR (Conventional Chest X-Ray) is the basic diagnostic tool. CXR may provide information regarding factors such as the size, shape, density and site of the lesion, apart from the existence of pleural effusions, alveolar or interstitial spread, collapse, lymphadenopathy, and rib metastases. An opacity is suspicious for malignancy if it has not calcified, has speculations, grows rapidly, or is >3 cm in diameter. There may also be hints about the histological type with Adenocarcinoma being peripheral, SCC central and large, and SCLC large, hilar, and with mediastinal lymphadenopathy. A lesion that has not grown in two years may be generally considered to be benign.

ii) CT (Computed Tomography) is a preferred modality for lung cancer diagnosis and staging. The injection of a contrast agent or material helps differentiate between blood vessels and lymph nodes. CT can offer better evaluation of the tumor's borders, the tumor's relation to neighboring structures, and the involvement of lymph nodes, bones, liver and adrenals.

Technical modifications of CT include: low-dose helical CT (spiral CT), HRCT—high Resolution CT and phase-contrast CT. Spiral CT provides higher spatial resolution than a CXR, at the expense however, of greater radiation exposure. For example, in conventional CT the radiation exposure may be greater by 10-100 than that in a CXR, while spiral CT exposes the subject to only 10-20% the exposure of conventional CT. CT allows scanning of the whole lung during a single breath-hold of 8-25 seconds. In functional CT, enhancement obtained by the contrast material is usually greater in malignant tumors due to the rich vascularity typical of malignant tissue. Typically, non-enhancement means no malignancy, although some benign tissues do enhance.

Currently, due to the common availability of CT, particularly of fast multislice CT scanners, CT remains the imaging gold standard for lung diagnosis. Promising results concerning the use of dynamic contrast enhanced CT were recently presented, using calculations of vascular parameters based on density-time curves. Perfusion values of lung nodules obtained by CT were found to agree with those obtained by PET, and to correlate with VEGF (vascular endothelial growth factor) levels.

Tumor perfusion has been found to be dependent on tumor size and localization, but not on histology. Furthermore, perfusion CT disclosed blood supply from both pulmonary and/or bronchial vessels in some tumors. In these dynamic studies both the spatial and temporal resolution were high but the scanning was limited to small volumes and short time span in order to minimize radiation hazards.

CT detects lesions that are greater than 2 mm, of which 45% are neoplastic. CT is superior to CXR because CT provides staging, volumetric, and density data (higher enhancement and size being more characteristic of malignancy), and evaluation of the best method to obtain a biopsy, including needle localization for biopsy under VATS (Video Assisted Thoracoscopic Surgery). Advancement in SPN (solitary pulmonary nodule) evaluation by CT has been made by improvements in image processing and computer assistance, named CAD (Computer-Aided Diagnosis).

iii) MRI (Magnetic Resonance Imaging) differentiates between solid and vascular structures, even without contrast material. Most importantly, MRI uses relatively harmless radio waves and there is no exposure to ionizing radiation as in CT. Due to longer acquisition time, patient movement is more detrimental.

The potential role of dynamic contrast enhanced ("DCE") MRI based evaluation of solitary pulmonary nodules was first described by Hittmair et al. The maximum enhancement and the initial velocity of contrast uptake were assessed and correlated with pathohistological findings. Malignant neoplastic SPNs enhanced stronger and faster than benign neoplastic SPNs.

More recently, additional DCE-MRI studies of SPNs confirmed the early results (Ohno Y, Hatabu H, Takenaka D, Adachi S, Kono M, Sugimura K. Solitary Pulmonary Nodules: Potential Role of Dynamic MR Imaging in Management Initial Experience Radiology, 2002 Aug; 224(2):503-11. See also, Fujimoto K, Abe T, Muller N L, Terasaki H, Kato S, Sadohara J, Kono R, Edamitsu O, Ishitake T, Hayashi A, Rikimaru T, Hayabuchi N., Small Peripheral Pulmonary Carcinomas Evaluated with Dynamic MR Imaging: Correlation with Tumor Vascularity and Prognosis, Radiology. 2003 Jun; 227(3): 786-93, Epub 2003 Apr. 24. Schaefer J F, Vollmar J, Schick F, Vonthein R, Seemann M D, Aebert H, Dierkesmann R, Friedel G, Claussen C. D. Solitary Pulmonary Nodules: Dynamic Contrast-Enhanced MR Imaging—Perfusion Differences in Malignant and Benign Lesions. Radiology. 2004 Aug; 232(2):544-53. Epub 2004 Jun. 23). The parameters measured were peak enhancement and slope of enhancement and in some studies wash-out ratio and time to maximum were added as well. In Fujimoto's study, the DCE-MRI parameters correlated with tumor vascularity suggesting a potential use for this method to predict prognosis.

The response of the vascular physiology to treatment of lung cancer was also assessed by DCE MRI (Hunter G. J., Hamberg L. M., Choi N, Jain R. K., McCloud T, Fischman A. J., Dynamic T1-Weighted Magnetic Resonance Imaging and Positron Emission Tomography In Patients with Lung Cancer: Correlating Vascular Physiology with Glucose Metabolism, Clin. Cancer Res. 1998 Apr; 4 (4):949-55).

The mean capillary permeability and surface area product (PS) in tumors was $0.0015+/-0.0002$ s$(-1)$ (n=13) before, $0.0023+/-0.0003$ s$(-1)$ (n=3, P=0.053) midway through, and $0.00075+/-0.0002$ s$(-1)$ (n=5, P<0.03) 2 weeks after treatment. Values for the extracellular contrast distribution space were $0.321+/-0.03$ before, $0.289+/-0.02$ midway through, and $0.195+/-0.02$ (P<0.01) 2 weeks after therapy. The glucose metabolic rate was significantly correlated with the PS product (P<0.01) but not with the extracellular contrast distribution space.

iv) PET (Positron Emission Tomography) using 18-fluorodeoxyglucose depicts increased glucose metabolism in tumor cells. This served to evaluate the primary tumor as well as regional lymph nodes and distant metastases.

Percutaneous needle biopsy, flexible fiberoptic bronchoscopy as well as surgical exploration offer additional diagnostic tools. However, they are characterized by inherent invasiveness. Recent developments include exhalation analysis of certain volatile organic compounds, cytological sputum analysis, immunostaining for hnRNP, A2/B1 or PGP9.5, and polymerase chain reaction-based assays for detecting tumor-specific mutations. Despite the various diagnostic modalities, 10-20% of patients undergo thoracotomy without prior pathologic diagnosis. The exact treatment regimen depends on precise histological data before treatment and after excision.

Early detection leads to better prognosis. For example, in stage I the survival is 60-70% and in stage Ia even higher. Unfortunately, only 15% of the cases are diagnosed at an early stage (I and II) when the tumor is well localized, so the overall survival has not risen lately. The one-year survival rate has increased from 32% in 1973 to 41% in 1994. However, the overall five-year survival rate is only 14%. Concerning lung metastases, the prognosis depends on the type of primary tumor and its biological behavior. For some carcinomas and sarcomas, the five-year survival after lung metastases excision is 25-45%.

The best chance of survival is expected when lung cancer presents incidentally on a CXR as a "coin lesion", or SPN, which is single, peripheral and asymptomatic. The SPN is defined as an abnormal round/oval density of diameter <=3 cm, surrounded by lung parenchyma and lacking cavitations or pulmonary infiltrates. There could be eccentric flecks of calcifications, but not broad or concentric ring calcifications. Approximately 80% of the coin lesions are malignant in patients of age >50 years. Only when the lesion has been known to exist for at least two years without enlarging and with a "benign" calcification pattern, could histological diagnosis be delayed.

Only about half of lesions suspicious enough to undergo an open biopsy turn out to be malignant. This brings about not only needless morbidity and mortality. The hospitalization costs of such a patient in the US are about $25,000. When a SPN is detected, it represents primary lung cancer in most breast cancer patients, and a metastasis in most melanoma patients. For cancer of the gastrointestinal tract the odds for both options are equal. Follow-up of a SPN is usually dependent upon the lesion's diameter:

1. <5 mm: HRCT after 3, 6, 12 & 24 months. Consider biopsy if enlarges. 1% malignancy.

2. 5-10 mm: as above, but 25-30% malignancy.

>10 mm: consider biopsy. 30-80% malignancy.

No fixed relationship exists between the size of the nodule and its biological behavior. It is possible that most patients already have metastases at the time of diagnosis, which the routine diagnostic tools do not always detect. This hypothesis is supported by clinical studies in which lymph nodes that appeared normal were found to contain metastases when evaluated by immunohistochemical staining or PCR (polymerase chain reaction).

There is general agreement among the various health organizations in the U.S., that the screening programs customary until recently (CXR and sputum cytology), have not contributed significantly to decrease the death rate. This is not true for the next three most common cancers: breast, prostate and colorectal, for which the death rate has decreased by 10-15% in the past 2 decades. It should also be noted, that in the Johns Hopkins Lung Project from the 70's, screening tests were negative in half of the patients that developed lung cancer, and became symptomatic before the next scheduled screening examination. A possible explanation was that some of the cases are so aggressive, that even strict follow-up and early detection will not increase survival. Actually, screening is intended mainly or NSCLC (75-80% of the cases), since SCLC is usually widely disseminated at presentation.

SUMMARY OF THE INVENTION

A method, system and computer-readable medium that provide a malignancy classification for a region of lung tissue are disclosed. The classifying operation includes some or all of the following: time points $T_1$ and $T_2$ measured from a time point $T_0$ at or near an injection of a contrast agent are set as described below. $T_1$ represents a wash-in time point for malignant lung tissue at which a first concentration value of the injected contrast agent is substantially equal to or near a peak for injected contrast agent concentration in the region of lung tissue. $T_2$ may be set such that a second concentration value of the injected contrast agent for malignant tissue is less than the first concentration value, and a third concentration value of the injected contrast agent for non-malignant tissue at $T_1$ is less than a fourth concentration value of the injected contrast agent concentration for the non-malignant tissue at $T_2$. Also $T_2$ may be set such that the second concentration value of the injected contrast agent for malignant tissue is substantially equal to the first concentration value, provided that the first concentration value exceeds a certain threshold value. Patient concentration values of the contrast agent for the area of lung tissue at time points $T_1$ and $T_2$ are obtained, and a malignancy classification for the region of lung tissue is provided by comparing the obtained sample concentration values with a predetermined malignancy profile. A visual representation of the malignancy classification of the region of lung tissue is outputted.

The time points may be set such that the second concentration value is greater than the fourth concentration value. Also, setting of the time points $T_1$ and $T_2$ may also include calculating concentration values of the injected contrast agent at initial time points $T_1$ and $T_2$, finding a maximum intensity for a calibration map comprising a grid with axes K and v, K representing a microvascular permeability value and v representing an extracellular volume value, and obtaining normalized intensity values of each grid point of the calibration map based on the maximum intensity; assigning one of multiple categories to each grid point based on a degree of change in concentration values between initial time point $T_1$ and initial time point $T_2$; and adjusting the calibration map such that grid points of a first category for grid points with a relatively high degree of change and grid points of a second category for grid points with a relatively low degree of change are approximately equally represented in the calibration map.

The assigning of the one of the three categories may be done, for example, by coloring or shading the grid point.

Further, $T_1$ and $T_2$ may be set such that the first classification is assigned to approximately 75% of grid points representing malignant tissue.

According to an aspect of the invention, the concentration values of the contrast agent are measured by a CT imaging machine.

The visual representation of the malignancy classification that is output may be color-coded image data. Also, the visual representation may be a voxel (volume pixel) representation, such that each pixel represents a volume of tissue.

The region of lung tissue may be evaluated based on the spatial distribution of malignant tissue in the visual representation.

Further, registration can be used to correct for shifting of the region of tissue in the obtaining of the concentration values. Also, in outputting of the visual representation smoothing based on surrounding pixels may be used to provide a more satisfactory image.

DETAILED DESCRIPTION OF THE INVENTION

The following discussion and the foregoing figures describe embodiments of Applicant's invention as best understood presently by the inventor however, it will be appreciated that numerous modifications of the invention are possible and that the invention may be embodied in other forms and practiced in other ways without departing from the spirit of the invention. Further, features of embodiments described may be omitted, combined selectively, or as a whole, with other embodiments, or used to replace features of other embodiments, or parts thereof, without departing from the spirit of the invention. The figures and the detailed description are therefore to be considered as an illustrative explanation of aspects of the invention, but should not be construed to limit the scope of the invention.

Before starting the evaluation of patient data, calibration of the imaging device may be necessary. For each contrast agent it may be necessary to calibrate according to the pharmacokinetic parameters in the blood. The following discussion will illustrate aspects of Applicant's invention with reference to data input from a CT imaging device and a contrast agent appropriate therefor. However, it will be understood that other such imaging data may be used to evaluate lung tissue.

The type of contrast agent used and its dose will depend on the type of imaging device from which imaging data is gathered. The relationship between the image data received, such as signal intensity and contrast agent concentration will depend on the type of contrast agent used. This information might be available from the company that provides the contrast material, or it can be independently measured as described below for the contrast agent Iopromide-Ultravist 300 (Shering).

For example, in a CT application, HU units (Hounsfield Units) measuring signal intensity S(t) are converted to Ultravist 300 concentration units (ml ultravist 300 solution/liter saline). The relationship between the measured signal intensity S(t) in HU and the concentration C(t) of contrast material (in ml per l) is described by:

$$S(t)=p+qC(t) \qquad (1)$$

where p and q are parameters to be determined.

Enhancement, E(t), is defined as the difference in signal intensities before and after contrast material injection:

$$E(t)=S(t)-S(t_0)=q[C(t)-C(t0)] \qquad (2)$$

The experimental factor that converts HU units to contrast material concentration units can be determined by preparing tubes with different concentrations of Ultravist 300 in normal saline. The tubes can then be scanned by the CT.

Figure 1:
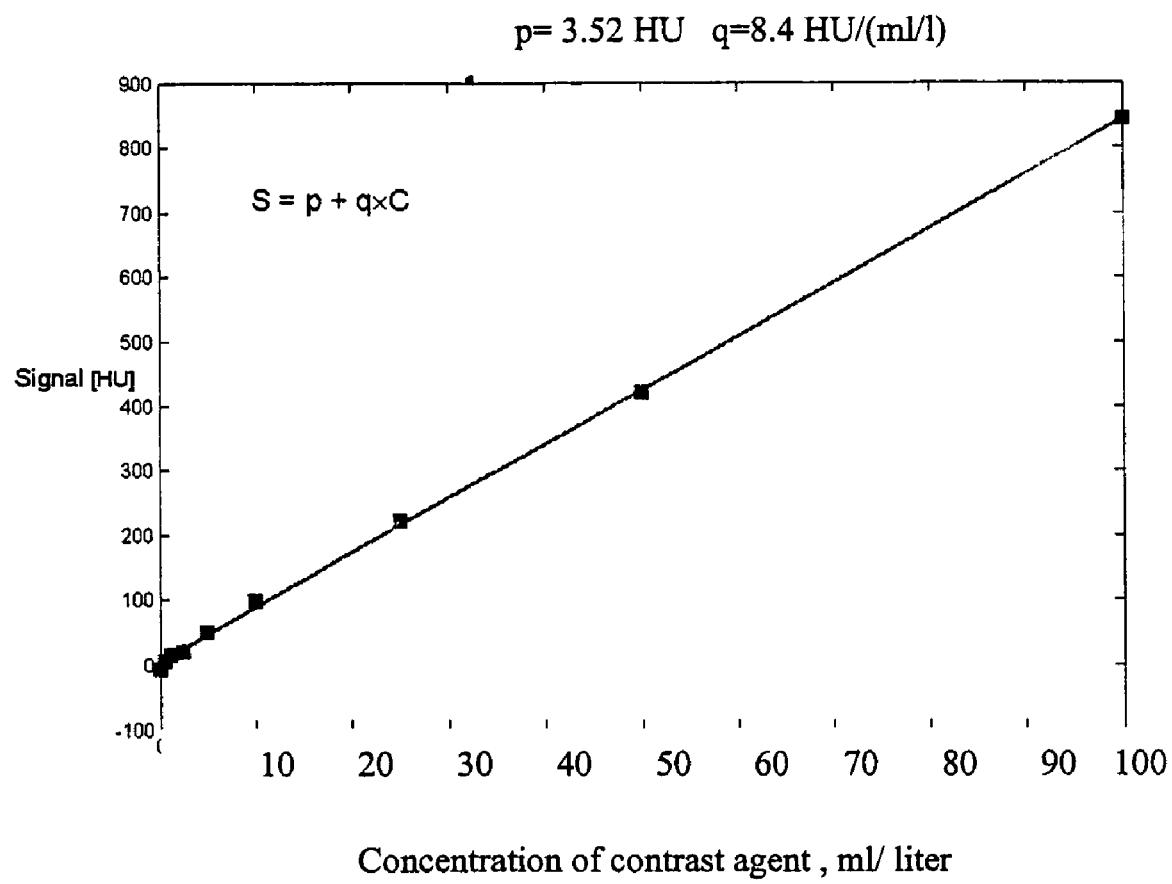
FIG. 1 shows a diagram illustrating a relationship between concentration of contrast agent and signal strength.

For example, for prepared concentrations, C (in ml Ultravist 300 per l saline), may be in the range of 0 to 2% (20 ml per l) which is approximately the concentration in the blood after the injection. FIG. 1 shows the signal intensity S of a central ROI obtained as part of the research study referred to herein, showing a calibration curve of iopromide (Ultravist 300 Shering) in saline solution, where the concentration of 1 ml/l corresponds to 0.1% iopromide in saline solution, hence, 10 ml/l corresponds to 1%. (The dose of 1.5 ml/kg in a 70 kg patient corresponds to ~20 ml/l, about 2% in blood.)

The present inventors calibrated the CT scanner as part of a research study. An explanation of the research study will illuminate aspects of the present invention. Thirty-four patients (22 men and 12 women; mean age 64 years; age range 47-82 years) were recruited from patients referred to the radiology department either from the Thoracic Surgery Ward, or from the Pulmonary Outpatient Clinic to undergo a CT scan as part of their further clinical evaluation of a lung lesion, prior to performing a biopsy. The biopsy could be obtained by thoracotomy, thoracoscopy, mediastinoscopy, bronchoscopy or transcutaneic. Exclusion criteria included abnormal kidney function tests, a known allergy to iodinet, age under 18 years, pregnancy and patients legally incapable of signing an informed consent. Informed consent was obtained according to the approval of the hospital's ethics committee.

All images were obtained using the Mx8000 (Philips) Multi Detector CT (MDCT) scanner in the Department of Radiology in Asaf-Harofeh Medical Center. Acquisition of the CT images was performed by an experienced technician under the surveillance of an expert radiologist. First, a surview scan of the chest was performed. This scan served to plan the study so it will focus on the lung lesion.

Consecutive scans of the lung lesion were then performed, with identical parameters. The first, prior to Intra-Venous contrast injection, and the next two at pre-determined time-points after contrast administration. The scan was performed with a 1.3 mm collimation (slice width) with a 1 mm slice interval, pitch 0.7, rot. time 0.75 sec, 120 kV tube voltage, 250 mAS. Voxel volume (pixel area×slice width) ranged between 0.78×0.78×1.3 mm³ (the majority) to 0.98×0.98×1.3 mm³.

The contrast agent for the CT was Iopromide (Ultravist 300; Schering) at a dose of 1.5 ml/kg, delivered through the antecubital vein at a rate of 3 ml/sec using an automatic injector (EnVision CT™). The patients were instructed to hold their breath following maximal expiration during the scanning, to decrease movement.

The contrast agent Iopromide (1 ml containing 0.623 g Iopromide) was selected for this study because it is a non-ionic water-soluble X-ray contrast medium with low osmotic pressure and better general tolerance compared to ionic contrast media. The contrast agent Iopromide has a molecular weight of 791.12 d (compared to 936 d of GdDTPA/dimeglumine). Iopromide is extremely hydrophilic and prevented from entering the intracellular lumen. Therefore, like Gd-DTPA, following IV administration iopromide is very rapidly distributed in the extracellular space, the half-life being 3 minutes, with an elimination half-life in patients of normal kidney function approximating 2 hours, irrespective of the dose (only 1.5% of the dosage is excreted in feces).

For each patient, the inventors recorded the signal intensity, S, of a central ROI in the aorta before contrast administration and at a selected time point after contrast injection. The inventors in the research study used the relation between HU and concentration units of Ultravist 300 (see above) to convert the measured enhancement to the corresponding concentration in the aorta, $C_p(t)$, assuming similar pharmacokinetics for all patients with normal kidney function. $C_p(t)$ in ml contrast agent per liter blood was fitted to the equation:

$$Cp(t)=D(a_1e^{-m_1t}+a_2e^{-m_2t})\ D\text{=dose in ml/kg (0.15 ml/kg)} \quad \text{Eq. 3}$$

to obtain: $a_1$=8.48 kg/l, $a_2$=7.34 kg/l, $m_1$=1.43 min$^{-1}$, $m_2$=0.1 min$^{-1}$.

Figure 2:
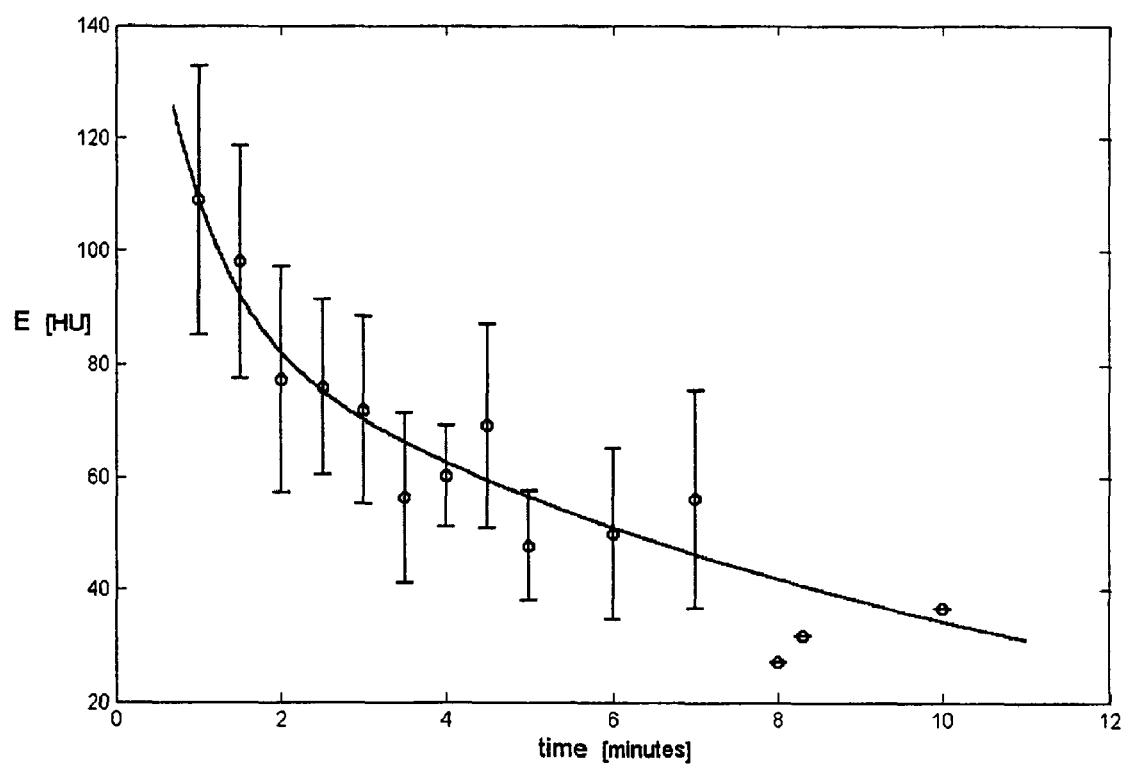
FIG. 2 illustrates enhancement expressed in Hounsfield Units representing signal strength as a function of time after contrast agent injection at a specified dose.

FIG. 2 illustrates enhancement (as defined in Eq. 2) in the aorta as a function of time after Iopromide (ultravist 300) injection at a dose of 0.15 ml/kg. The decay in the enhancement followed eq. 3 using the concentration to enhancement conversion (equation 2).

The exchange of contrast material between the intravascular and extravascular extracellular volumes in each pixel of the tumor is dependent upon two parameters: the influx transcapillary transfer constant $k_{in}$ and the efflux transcapillary constant $k_{ep}$. The latter constant is equal to the outflux transcapillary constant $k_{out}$ divided by the effective extracellular volume fraction $v_e$. The division by $v_e$ stems from the fact that the contrast material cannot enter the cells and is therefore leaking solely to the extracellular interstitial spaces. When the transfer constant from the capillaries to the interstitial spaces and back are equal, namely $k_{in}=k_{out}$, then $k_{in}/k_{ep}$=ve. Hence $k_{in}$ and $v_e$ are two independent parameters that determine the contrast enhancement time course.

Furthermore, $k_{in}$ depends on both the blood flow rate and the vessel permeability. When the blood flow per pixel is much faster than the vessel permeability (P) times surface area (S) per unit volume (V), PS/V, $k_{in}$ values are determined by the multiplicity PS.

The solution to the differential equation that describes the concentration of contrast agent at time t after a bolus contrast administration, for $k_{in}=k_{out}$ is given by the following equation (24):

$$C_t(t)=D(b_1e^{-m_1t}+b_2e^{-m_2t}+b_3e^{-m_3t}) \quad (4)$$

where $b_1=k_{in}\ a_1/(k_{in}/v-m_1)$, $b_2=k_{in}\ a_2/(k_{in}/v-m_2)$, $b_3=-(b_1+b_2)$ and $m_3=k_{in}/v_e$.

This equation represents an initial increase of $C_t(t)$ with time, as the contrast material is transferred from the blood vessels into the tumor's extracellular space, followed by a decrease as the contrast agent is cleared from the tumor back to the blood. Note, that eq. (4) approaches eq. (3) when $k_{in}\rightarrow\infty$ and $v_e$=1 as occurs in blood.

Figure 6:
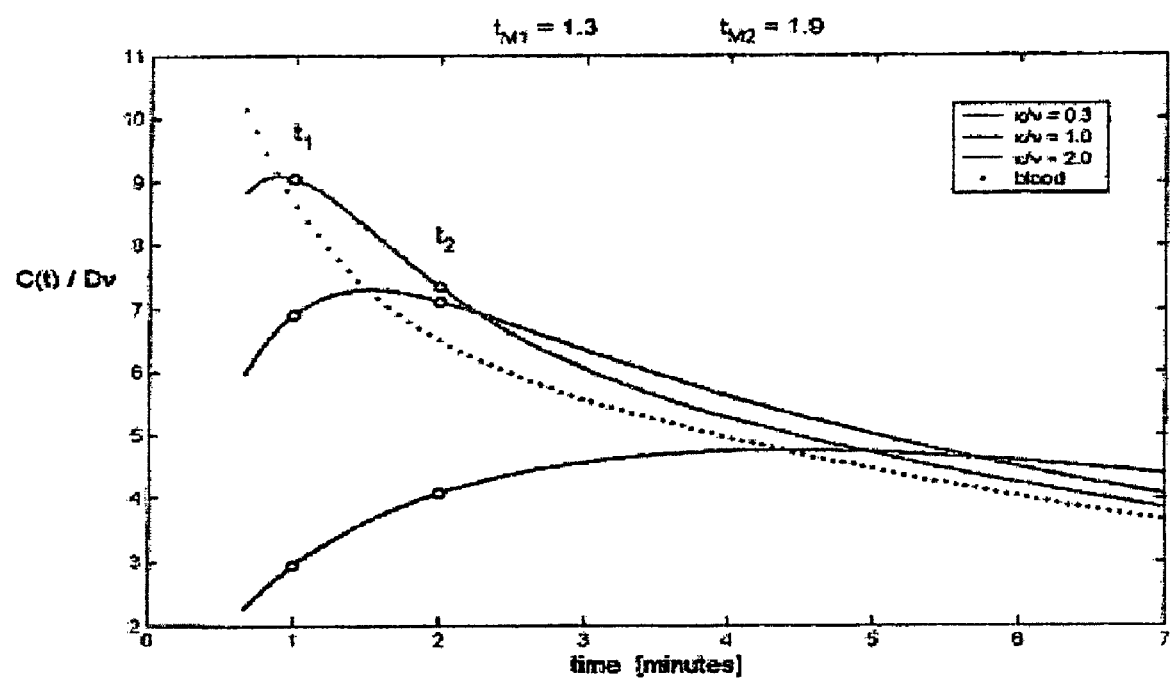
FIG. 6 is a chart illustrating the variation of contrast agent concentration (y-axis) as a function of time (x-axis) for three lung tissue profiles, and for blood.

FIG. 6 is a chart illustrating the variation of contrast agent concentration (y-axis) as a function of time (x-axis) for three lung tissue profiles, and for blood (dotted curve), with two time points $T_1$ and $T_2$. The upper solid curve is an example of a profile for malignant tissue, which is near its peak at $T_1$. The lower most solid curve is an example of non-malignant tissue.

Using the above pharmacokinetics parameters for ultravist 300, equation 4, two selected post contrast time points, and the color coding scheme based on three colors for washout patterns and color intensity for initial rate of enhancement (FIG. 3), it is possible to calculate for the selected time points for each pair of $k_{in}$ and $v_e$ a color hue and intensity which yields the appropriate calibration map.

Figure 4A:
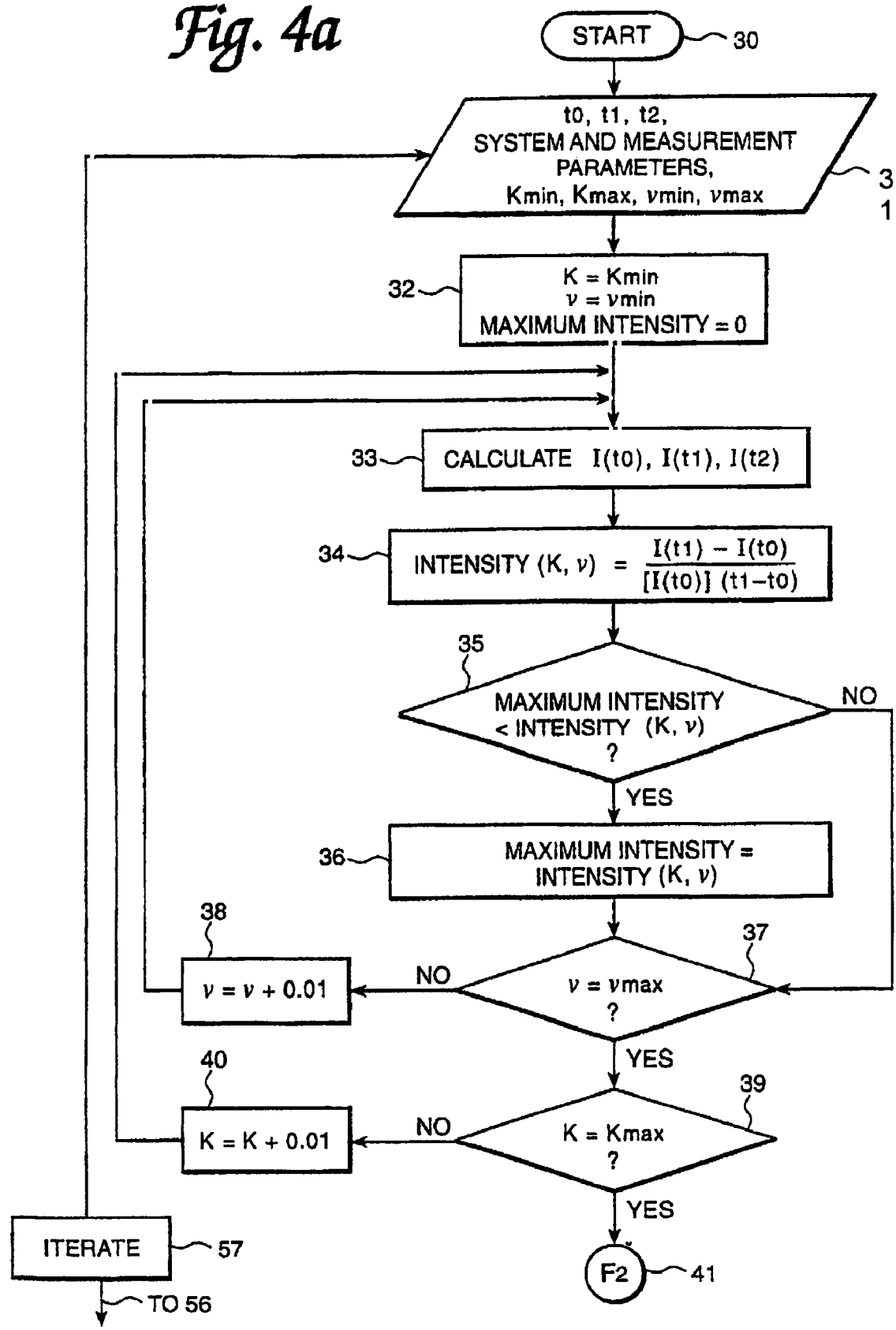
FIGS. 4a-4b show a flow diagram for preparation of a calibration map, according to an aspect of the invention.

FIG. 4 shows a flow diagram as an example of a method for setting the parameters for data collection and creating a calibration map. This flow diagram shows that concentration of the contrast agent varies with time as a function of two variables of the system assigned here with the letters K and v. The pharmacokinetics parameters define the contrast agent change with time in the blood. The variable K defines microvascular permeability which estimates the capacity of blood vessels to leak out the tracer. The variable v defines the fraction of extracellular volume which estimates the amount of free space in a tissue. For each grid point in a 2 dimensional grid of K and v, a pixel of dimension of 0.01 units of K and 0.01 units of v is defined at blocks 38, 40, 53 and 55.

Figure 5:
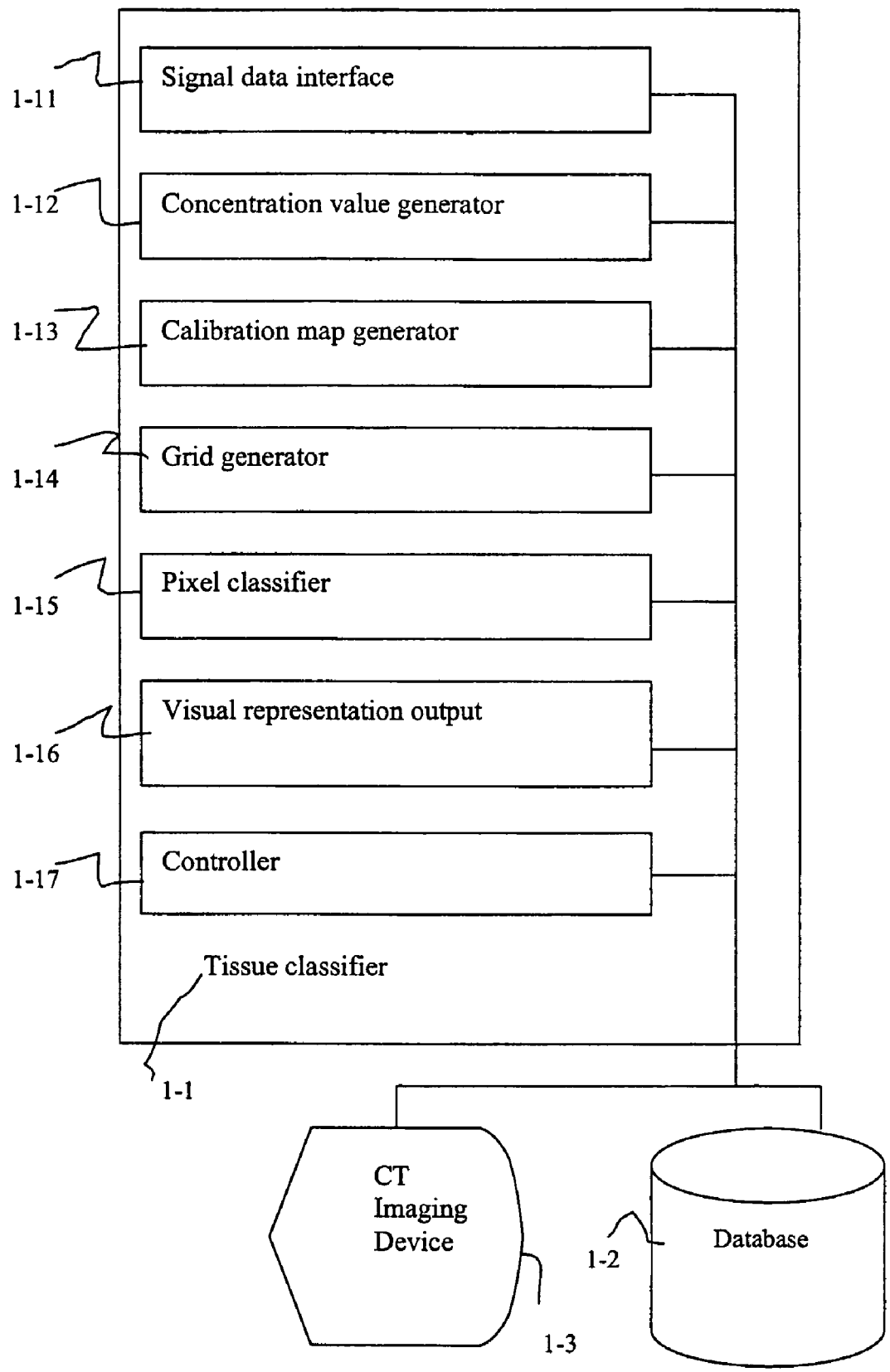
FIG. 5 is a schematic diagram of a tissue classifier.

The program starts at block 30 and gets inputs of the time points, $t_0$, $t_1$ and $t_2$, system and measurement parameters and the range of K and the range of v values between their minimum and maximum values in block 31. As shown in FIG. 5, the signal values are fed to signal data interface 1-11 of the tissue classifier 1-1 from the CT imaging device 1-3 or other such imaging device. It will be understood that the entire tissue classifier 1-1, or one or more portions or modules thereof, may be physically or logically integrated with the CT imaging device 1-3 as a software, hardware, firmware, or other such component or module of the CT imaging device 1-3, or the tissue classifier 1-1, or one or more portions thereof, may be connected via a wired or wireless connection with the CT imaging device 1-3.

The data may be saved in database 1-2. Database 1-2 may be physically or logically integrated with the tissue classifier 1-1 and/or with the CT imaging device or may be connected thereto via a wired or wireless connection. Controller 1-17 may control the input/output of the tissue classifier 1-1, its interface with the CT imaging device 1-3 and with a human operator, and may control overall functioning of the tissue classifier 1-1. Concentration value generator 1-12 converts the signal intensities to concentration values, according to a function (or lookup table) of the type shown in FIG. 1. Alternatively, the CT or imaging device may already feed the concentration values to the tissue classifier 1-1, instead of just the signal strength data.

Calibration map generator 1-13, or grid generator 1-14 as a module of calibration map generator 1-13, starts from pixel (K min, v min) in block 32 to calculate $I(t_0)$, $I(t_1)$, $I(t_2)$ in block 33, estimating how the concentration varying with time I(t) depends on K and v, and on other system parameters. The determined or calculated I(t1) and I(t0) are used to calculate for each pixel Intensity (K, v) as shown in block 34, which represent wash-in initial rate, at least for malignant tissue.

Figure 4B:
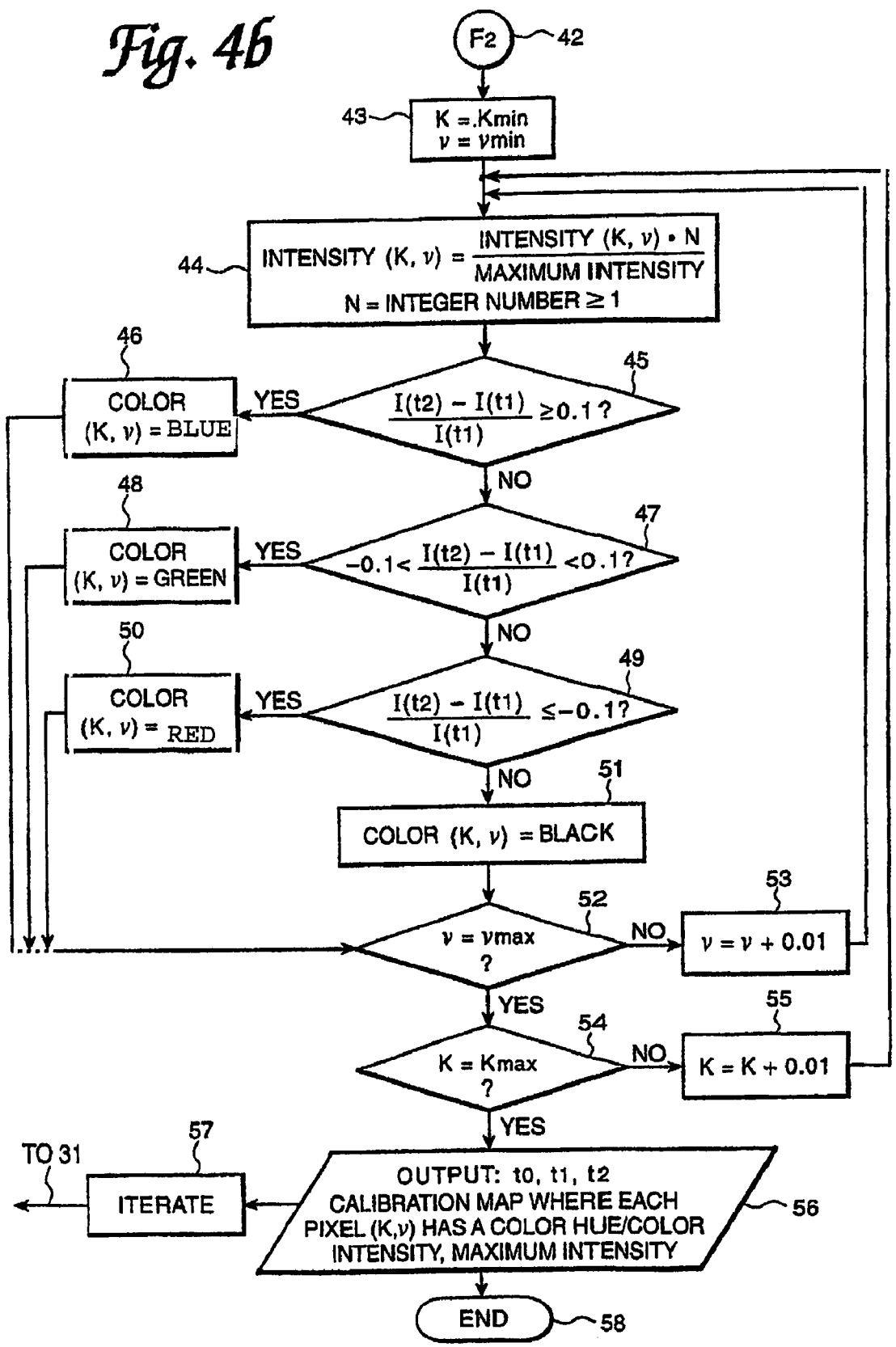

The calibration map generator 1-13 controls a search for the pixel that has maximum intensity (blocks 35 to 40) and proceeds through all the pixels loop-wise returning to block 33 and going again through the steps 34 to block 40 until it reaches the pixel with maximum K and maximum v. Through this search process, the pixel with maximum intensity is identified and intensity is calculated for all pixels (K, v). In FIG. 4b, the program proceeds to calculate for each pixel starting from pixel (K min, v min) block 43 a normalized intensity, normalized relative to the maximum intensity, as shown at block 44. The pixel with maximum intensity is assigned a maximum value for intensity N. N can be 1, 2, 3 or any number such as, 8, 64, 256 (computer numbers), etc. depending on the demands of the system.

Figure 3:
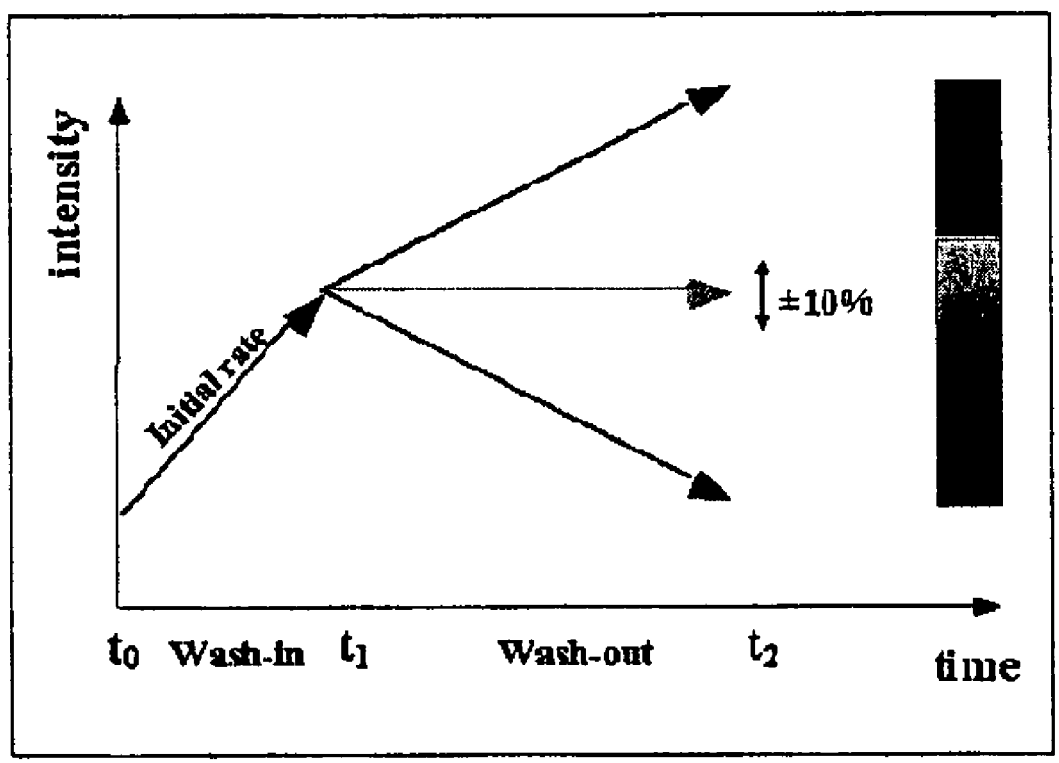
FIG. 3 shows a diagram for classifying a pixel (assigning one of three colors) based on wash-out rate, according to an aspect of the invention.

Then, pixel classifier 1-15 calculates the wash-out pattern for each pixel starting from pixel (K min, v min) until it reaches pixel (K max, v max) and codes with color hue each pattern as shown in blocks 45 to 54. As shown in FIG. 3, according to an aspect of the present invention, color or hue of the pixel shows the change in intensity between $t_1$ and $t_2$ for that pixel. When the intensity $I(t_2)$ is less than $I(t_1)$, the color hue is red, when the reverse holds the color is blue and when the intensity is equal or close to equal, it is green. Most malignant tissue will be shown as red pixels, and most non-malignant tissue will be shown as blue. It will be understood that other colors may be used in addition to the foregoing or instead of the foregoing. Also, other types of visual representations, such as shading or the like may be used instead of or in addition to colors. The definitions of higher lower and equal intensities depend on the noise level, and can be adjusted to be above the noise level.

Figure 7A:
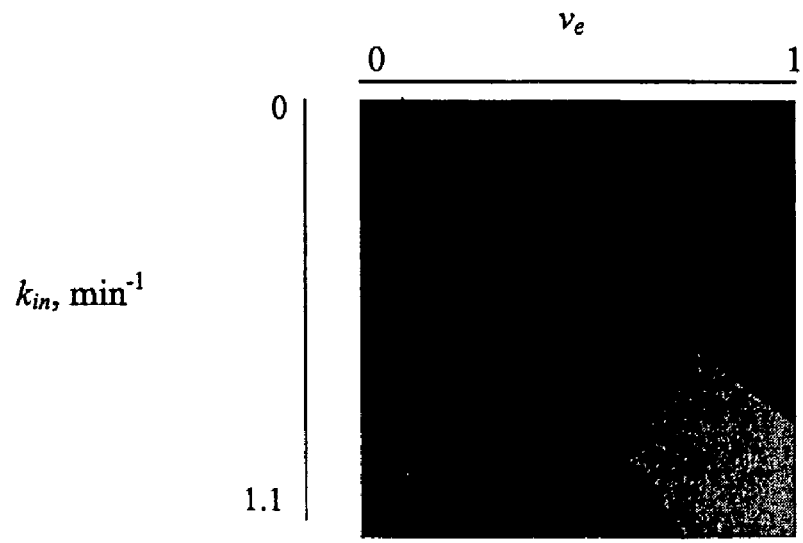
FIGS. 7a and 7b show examples of calibration charts with different maximum K values according to an aspect of the present invention.
Figure 7B:
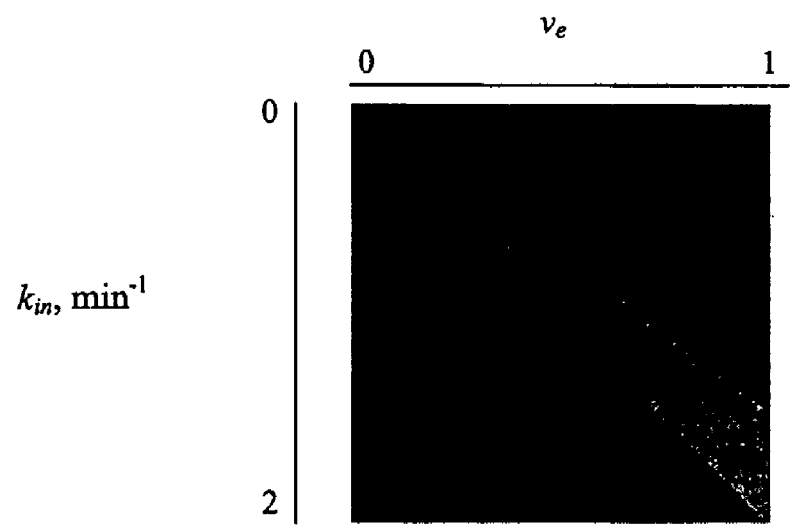

Continuing with the example of the calibration map generation process illustrated in FIG. 4, at this point, all pixels have a color hue and a normalized color intensity. Visual representation output 1-16 produces in block 56 of FIG. 4b as the output a calibration map of K, v for the selected $t_0$, $t_1$, $t_2$ and system and measurement parameters. The output consists of a calibration map of the two variables K and v ranging between K min, v min to K max, v max for a specific set of time points and the other inputs. Each pixel in this map with specific K, v values has a color hue and a color intensity. FIGS. 7a and 7b are examples of color-coded (in black and white) calibration maps with the red region shown on the left lower portion with more pixels in the higher K, lower v range, and blue region shown on the right upper portion with more pixels in the lower K, higher v range.

If the calibration map is not satisfactory, for example, if it is excessively slanted toward one color hue, new time points are chosen in a direction to correct the calibration map and bring it to a more satisfactory balance from a color distribution standpoint. Accordingly, in subsequent iterations, the program cycles through the steps in the flow diagram again using the new inputs until a satisfactory calibration map is obtained, which sets the selected time points and system parameters. A satisfactory calibration map is defined by reaching a certain distribution of the colors or of the colors and color intensities. For example, a satisfactory map can be a map that divides the K-v plane, or volume between the three colors to approximately three equal areas, namely, approximately a third of the pixels in the calibration map are red, a third are green and a third are blue. Also, new time points $t_1$ and $t_2$ may be selected to arrive at a calibration map such that the red color is assigned to approximately 75% of grid points representing malignant tissue.

For lung CT with Ultravist 300 at a dose of 1.5 ml/kg we found that the major three time points are: pre contrast ($t_0$) and two post contrast time points:

$(t_1) = 1$ min and $(t_2) = 2$ min

The calibration map for these three time points for ultravist 300 at the dose of 1.5 ml/kg taking the limits for $k_{in}$ between 0 and 1.1 min$^{-1}$ (the upper limit is on the basis of the studies of patients with lung cancer and present the median of the values obtained for lung cancers) is presented below in FIG. 7a:

The additional three time points recommended for improving diagnosis use ($t_0$) and ($t_2$)=2 min and add ($t_{0.5}$)=0.5 min. These three time points are designed to fit the high $k_{in}$ found in the lung because of the fast flow and high vascularization of this organ and presents the upper limit for this parameter which is 2 min$^{-1}$. The calibration map for the three time points $t_0$, $t_{0.5}$ and $t_2$, ultravist 300 at the dose of 1.5 ml/kg and $k_{in}$ ranging from 0 to 2 min$^{-1}$ is given below in FIG. 7b.

In the research study conducted by the present inventors, analysis and statistical evaluation was done with special attention to the extent of pixels colored, the extent of pixels exhibiting each color hue; the brightness range, and the spatial distribution of the different colors (hue and brightness). Altogether, 34 patients were enrolled in the study of whom one had two separate right lung lesions and five were found unfit to undergo image analysis due to technical acquisition problems. Therefore, a total of 30 lung lesions of variable diagnoses was collected. The tumor size ranged from 2×1.6× 0.5 to 7.8×7×12.4 cm$^3$ with the majority under 5 cm largest diameter. Their final diagnoses (except one with macrophages per cytology waiting for another biopsy) are presented in Table 1:

TABLE 1

Pathological diagnoses of the lung lesions enrolled in the study.

| | | | | Diagnosis* | | | | | | |
|---|---|---|---|---|---|---|---|---|---|---|
| | MFH | SCLC | Ly | Breast met. | MM | NSCLC sub-type undefined | NSCLC SCC | NSCLC LCC | NSCLC Adeno-carcinoma | SFT | Benign |
| Number of patients | 2 | 2 | 1 | 1 | 1 | 5 | 5 | 1 | 6 | 1 | 4 |

MFH—metastatic Malignant Fibrous Histiocytoma; Ly—Lymphoma; Breast met.—Breast metastasis; MM—Multiple Myeloma; SFT—Solitary Fibrous Tumor.

Another difference is that through coloring of the central pixels in the malignant tumor, most of the colored pixels of the benign lesion are on its contour. Coloring of the tumor's borders is usually the result of movement of the tumor between $t_0$ and $t_1$. Since the enhanced tumors are surrounded by normal lung tissue containing air (black in CT), the difference in enhancement intensity in a pixel between $t_0$ and $t_1$ can be large on behalf of movement of the tumor to an area of normal lung tissue (or vice versa). This occurs mainly along the contour of the tumor.

During image analysis it was found, that the area containing the tumor within the CT image moved between different time points, mostly due to thoracic breathing movement. The amount of movement in the z direction was evaluated by looking at sequential slices of the tumor in the three different time points on the screen, and forming triplets of the same slice at the three time points.

Movement in the x-y direction was initially evaluated by putting a semi-transparent slice on top of its corresponding slice at a different time point and moving it until the best fit was found. The amount of movement in the x and y direction was recorded, and inserted into specially developed software which shifted all the pixels in the slice by the assigned amount. Later in the course of our study, an automatic registration algorithm was developed. Movement in the x-direction ranged between 0-20 pixels and in the y-direction between 0-12 pixels, both with a median of 2 pixels. This algorithm does not take into account rotation, angulation, shrinkage or enlargement of the tumor, which we ignored and presumed minimal. It will be understood that registration may be accomplished in several known ways, if it is to be performed at all, without departing from the spirit of the present invention.

The inventors also tested the application of "smoothing"; the color hue and intensity of each pixel was assigned after taking into account the values of the eight surrounding pixels as well. According to an embodiment of the present invention, smoothing is used based on four or more surrounding pixels to provide for an enhanced visual representation. It will be understood that several known smoothing methods may be used to perform smoothing according to this embodiment of the invention.

Tables 2 and 3 show statistical analysis of the study results. Table 2 contains the benign results. Table 3 contains the malignant results.

TABLE 2

| | Benign SPNs | | | |
|---|---|---|---|---|
| Patient | % VOL | R | R' | Intensity |
| 1 | 34 | 58 | 20 | 0.52 |
| 2 | 38 | 34 | 13 | 0.39 |
| 3 | 2 | 100 | 3 | 0.63 |
| Average | 25 | 64 | 12 | 0.51 |

Percent Vol - percent of the colored out of the total tumors' pixels
R - percent of the Red pixels out of the total colored tumor pixels
R'- percent of the red pixels out of the total pixels of the tumor
Intensity - average value of color-intensity

TABLE 3

Malignant Tumors from the Upper Left to the Lower Right Corner.

| Patient | % Vol | R | R' | Intensity |
|---|---|---|---|---|
| 1 | 87 | 54 | 47 | 0.72 |
| 2 | 85 | 65 | 55 | 0.74 |
| 3 | 60 | 40 | 24 | 0.42 |
| 4 | 93 | 55 | 51 | 0.81 |
| 5 | 100 | 41 | 41 | 0.67 |
| 6 | 84 | 69 | 57 | 0.79 |
| 7 | 84 | 40 | 34 | 0.75 |
| 8 | 89 | 47 | 42 | 0.78 |
| 9 | 81 | 56 | 45 | 0.86 |
| Average | 85 | 52 | 44 | 0.73 |

The present study shows that the method disclosed herein can distinguish readily between a benign and malignant SPN using the 3TP-CT method. The gross differences include: higher fraction of colored tumor pixels in the malignant as opposed to the benign tumors; higher percentage of the tumor's pixels being colored in red in the malignant versus the benign tumors; higher color-intensity in the malignant versus the benign tumors.

While preferred embodiments of the invention have been described, it will be understood that various modifications and changes in form or detail could readily be made without departing from the spirit of the invention. It is therefore intended that the invention be not limited to the exact forms described and illustrated, but should be construed to cover all modifications that may fall within the scope of the appended claims.

What is claimed is:

1. A method of providing a malignancy classification for a region of lung tissue, the method comprising:
   setting time points $T_1$ and $T_2$ measured from a time point $T_0$ at or near an injection of a contrast agent, $T_1$ representing a wash-in time point for malignant lung tissue at which a first concentration value of the injected contrast agent is substantially equal to or near a peak for injected contrast agent concentration for the malignant lung tissue, wherein at $t_2$ a second concentration value of the injected contrast agent for the malignant lung tissue is less than or substantially equal to the first concentration value at $T_1$, and a third concentration value of the injected contrast agent for non-malignant lung tissue at $T_1$ is less than or substantially equal to a fourth concentration value of the injected contrast agent concentration for the non-malignant lung tissue at $T_2$;

wherein the setting of the time points $T_1$ and $T_2$ is determined from degree of changes in concentration values in the region of the lung tissue between time points $T_1$ and $T_2$ satisfying a preselected condition based on a maximum intensity predicated on microvascular permeability and extracellular volume of the region of lung tissue;

obtaining a first sample concentration value of the contrast agent for the region of lung tissue at $T_1$ and a second sample concentration value of the contrast agent for the region of lung tissue at T2;

determining a malignancy classification for the region of lung tissue by comparing the obtained sample concentration values with a predetermined malignancy profile; and outputting a visual representation of the malignancy classification of the region of lung tissue.

2. The method of claim 1, wherein the second concentration value is greater than the fourth concentration value.

3. The method of claim 1, wherein said determining the malignancy classification comprises judging that the region of lung tissue contains malignancy when the first obtained sample concentration value is greater than the second obtained sample concentration value.

4. The method of claim 1, wherein said determining the malignancy classification comprises judging that the region of lung tissue contains malignancy when the first obtained sample concentration value is substantially equal to the second obtained sample concentration value, and the first obtained sample concentration value is higher than a predetermined first threshold concentration value.

5. The method of claim 1, wherein said determining the malignancy classification comprises judging that the region of lung tissue contains no malignancy when the first obtained sample concentration value is less than the second obtained sample concentration value.

6. The method of claim 1, wherein said determining the malignancy classification comprises judging that the region of lung tissue contains no malignancy when the first obtained sample concentration value is substantially equal to the second obtained sample concentration value, and the first obtained sample concentration value is less than a predetermined second threshold concentration value.

7. The method of claim 1, wherein the setting of the time points $T_1$ and $T_2$ comprises:

calculating concentration values of the injected contrast agent at initial time points $T_1$ and $T_2$;

finding a maximum intensity for a calibration map comprising a grid with axes K and v, K representing a microvascular permeability value and v representing an extracellular volume value, and obtaining normalized intensity values of each grid point of the calibration map based on the maximum intensity;

assigning one of multiple categories to each grid point based on a degree of change in concentration values between initial time point $T_1$ and initial time point $T_2$;

adjusting the calibration map such that grid points of a first category for grid points with a relatively high degree of change and grid points of a second category for grid points with a relatively low degree of change are approximately equally represented in the calibration map.

8. The method of claim 7, wherein a third category of the multiple categories is assigned to grid points with a degree of change within a predetermined range, the predetermined range being based on a noise level relative to signal strength.

9. The method of claim 8, wherein the predetermined range comprises a range of percent change substantially equal to the noise level relative to signal strength.

10. The method of claim 8, wherein the degree of change falling within the predetermined range is plus or minus 10%.

11. The method of claim 7, wherein said assigning of the one of the multiple categories comprises at least one of coloring and shading the grid point.

12. The method of claim 7, wherein $T_1$ and $T_2$ are set such that the first classification is assigned to approximately 75% of grid points representing malignant tissue.

13. The method of claim 1, wherein the concentration values of the contrast agent are measured by CT.

14. The method of claim 1, wherein the visual representation of the malignancy classification is color-coded image data.

15. The method of claim 1, wherein the visual representation is a voxel representation.

16. The method of claim 1, wherein the region of lung tissue is evaluated based on the spatial distribution of malignant tissue in the visual representation.

17. The method of claim 1, wherein registration is used to correct for shifting of the region of tissue in obtaining the concentration values.

18. The method of claim 1, wherein said outputting of the visual representation comprises smoothing based on surrounding pixels.

19. The method of claim I wherein the setting of the time points $T_0$, $T_1$ and $T_2$ is determined from degree of changes in concentration values in the region of the lung tissue between time points $T_0$ and $T_1$ and between time points $T_1$ and $T_2$ satisfying a preselected condition based on a maximum intensity predicated on microvascular permeability and extracellular volume of the region of lung tissue.

20. A computer-readable medium incorporating a program of instructions for providing a malignancy classification for a region of lung tissue, the program of instructions comprising:

instructions for setting time points T1 and t2 measured from a time point T0 at or near an injection of a contrast agent, T1 representing a wash-in time point for malignant lung tissue at which a first concentration value of the injected contrast agent is substantially equal to or near a peak for injected contrast agent concentration for the malignant lung tissue, wherein at T2 a second concentration value of the injected contrast agent for the malignant lung tissue is less than or substantially equal to the first concentration value at T1, and a third concentration value of the injected contrast agent for non-malignant lung tissue at T1 is less than or substantially equal to a fourth concentration value of the injected contrast agent concentration for the non-malignant lung tissue at T2;

wherein the setting of the time points T1 and T2 is determined from degree of changes in concentration values in the region of the lung tissue between time points T1 and T2 satisfying a preselected condition based on a maximum intensity predicated on microvascular permeability and extracellular volume of the region of lung tissue;

instructions for obtaining a first sample concentration value of the contrast agent for the region of lung tissue at T1 and a second concentration value of the contrast agent for the region of lung tissue at T2;

instructions for determining a malignancy classification for the region of lung tissue by comparing the obtained sample concentration values with a predetermined malignancy profile; and instructions for outputting a visual representation of the malignancy classification of the region of lung tissue.

21. The medium of claim 20, wherein the second concentration value is greater than the fourth concentration value.

22. The medium of claim 20, wherein said instructions for determining the malignancy classification comprise instructions for judging that the region of lung tissue contains malignancy when the first obtained sample concentration value is greater than the second obtained sample concentration value.

23. The medium of claim 20, wherein said instructions for determining the malignancy classification comprise instructions for judging that the region of lung tissue contains malignancy when the first obtained sample concentration value is substantially equal to the second obtained sample concentration value, and the first obtained sample concentration value is higher than a predetermined first threshold concentration value.

24. The medium of claim 20, wherein said instructions for determining the malignancy classification comprise instructions for judging that the region of lung tissue contains no malignancy when the first obtained sample concentration value is less than the second obtained sample concentration value.

25. The medium of claim 20, wherein said instructions for determining the malignancy classification comprise instructions for judging that the region of lung tissue contains no malignancy when the first obtained sample concentration value is substantially equal to the second obtained sample concentration value, and the first obtained sample concentration value is less than a predetermined second threshold concentration value.

26. The medium of claim 20, wherein said instructions for setting of the time points $T_1$ and $T_2$ comprises:

instructions for calculating concentration values of the injected contrast agent at initial time points $T_1$ and $T_2$;

instructions for finding a maximum intensity for a calibration map comprising a grid with axes K and v, K representing a microvascular permeability value and v representing an extracellular volume value, and obtaining normalized intensity values of each grid point of the calibration map based on the maximum intensity;

instructions for assigning one of multiple categories to each grid point based on a degree of change in concentration values between initial time point $T_1$ and initial time point $T_2$;

instructions for adjusting the calibration map such that grid points of a first category for grid points with a relatively high degree of change and grid points of a second category for grid points with a relatively low degree of change are approximately equally represented in the calibration map.

27. The medium of claim 26, wherein a third category of the multiple categories is assigned to grid points with a degree of change within a predetermined range, the predetermined range being based on a noise level relative to signal strength.

28. The medium of claim 27, wherein the predetermined range comprises a range of percent change substantially equal to the noise level relative to signal strength.

29. The medium of claim 27, wherein the degree of change falling within the predetermined range is plus or minus 10%.

30. The medium of claim 26, wherein said assigning of the one of the three categories comprises at least one of coloring and shading the grid point.

31. The medium of claim 26, wherein $T_1$ and $T_2$ are set such that the first classification is assigned to approximately 75% of grid points representing malignant tissue.

32. The medium of claim 20, wherein the concentration values of the contrast agent are measured by CT.

33. The medium of claim 20, wherein the visual representation of the malignancy classification is color-coded image data.

34. The medium of claim 20, wherein the visual representation is a voxel representation.

35. The medium of claim 20, wherein the region of lung tissue is evaluated based on the spatial distribution of malignant tissue in the visual representation.

36. The medium of claim 20, wherein registration is used to correct for shifting of the region of tissue in obtaining the concentration values.

37. The medium of claim 20, wherein said outputting of the visual representation comprises smoothing based on surrounding pixels.

38. The computer readable medium of claim 20 wherein the setting of the time points $T_0$, $T_1$ and $T_2$ is determined from degree of changes in concentration values in the region of the lung tissue between time points $T_0$ and $T_1$ and between time points $T_1$ and $T_2$ satisfying a preselected condition based on a maximum intensity predicated on microvascular permeability and extracellular volume of the region of lung tissue.

* * * * *